(12) United States Patent  
Kim et al.

(10) Patent No.: US 11,408,996 B2  
(45) Date of Patent: Aug. 9, 2022

(54) ULTRASONIC IMAGING APPARATUS AND METHOD OF CONTROLLING THE SAME

(71) Applicant: SAMSUNG MEDISON CO., LTD., Gangwon-do (KR)

(72) Inventors: Kang Sik Kim, Seongnam-si (KR); Tai-Kyong Song, Seoul (KR); Sung Ho Kim, Seoul (KR); Sua Bae, Seoul (KR); Hyunwoo Song, Seoul (KR); Jintae Jang, Seoul (KR)

(73) Assignee: SAMSUNG MEDISON CO. LTD., Gangwon-Do (KR)

( * ) Notice: Subject to any disclaimer, the term of this patent is extended or adjusted under 35 U.S.C. 154(b) by 566 days.

(21) Appl. No.: 16/524,524

(22) Filed: Jul. 29, 2019

(65) Prior Publication Data

US 2020/0033471 A1    Jan. 30, 2020

(30) Foreign Application Priority Data

Jul. 30, 2018  (KR) .................. 10-2018-0088542

(51) Int. Cl.
- *G01S 15/46* (2006.01)
- *G01S 15/89* (2006.01)
- *G01S 7/52* (2006.01)

(52) U.S. Cl.
CPC .......... *G01S 15/46* (2013.01); *G01S 7/52046* (2013.01); *G01S 7/52084* (2013.01); *G01S 15/8906* (2013.01)

(58) Field of Classification Search
CPC .. G01S 15/46; G01S 7/52046; G01S 7/52084; G01S 15/8906; G01S 7/52047; G01S 7/52073; G01S 15/8997; G01S 15/8915; A61B 8/461; A61B 8/467; A61B 8/469; A61B 8/5207; A61B 8/54

See application file for complete search history.

(56) References Cited

U.S. PATENT DOCUMENTS

| 6,544,179 B1 | 4/2003 | Schmiesing et al. |
| 2016/0174938 A1 | 6/2016 | Takano |

(Continued)

FOREIGN PATENT DOCUMENTS

| EP | 3207878 A1 | 8/2017 | |
| EP | 3605143 A1 * | 2/2020 | ............. A61B 8/461 |

(Continued)

OTHER PUBLICATIONS

European Communication dated Nov. 15, 2021 issued in European Patent Application No. 19188886.6.

(Continued)

*Primary Examiner* — Daniel Pihulic (74) *Attorney, Agent, or Firm* — Morgan, Lewis & Bockius LLP (57) ABSTRACT

Provided is an ultrasonic imaging apparatus including: an inputter configured to receive an input of a region of interest (ROI) from a user; a beamformer configured to perform transmission/reception focusing with respect to a virtual source to be used for a synthetic aperture focusing method; a display; and a main controller configured to determine a position of the virtual source on the basis of an image quality in the received ROI and control the display to display the determined position of the virtual source.

18 Claims, 11 Drawing Sheets

(56) References Cited

U.S. PATENT DOCUMENTS

2020/0033471 A1* 1/2020 Kim .................... A61B 8/5207
2021/0295816 A1* 9/2021 Kim .................... G01S 7/5202

FOREIGN PATENT DOCUMENTS

| EP | 3838161 A1 * | 6/2021 | ........... A61B 8/4477 |
| KR | 10-2011-0022445 A | 3/2011 | |
| KR | 10-2014-0102995 A | 8/2014 | |
| KR | 10-1627821 B1 | 6/2016 | |
| WO | 2019/077937 A1 | 4/2019 | |

OTHER PUBLICATIONS

Extended European Search Report dated Dec. 6, 2019 issued in European Patent Application No. 19188886.6.
Kim Choye, et al., "Evaluation of Ultrasound Synthetic Aperture Imaging Using Bidirectional Pixel-Baed Focusing: Preliminary Phantom and In Vivo Breast Study," IEEE Transactions on Biomedical Engineering, vol. 60, No. 10, Oct. 2013, pp. 2716-2724.

* cited by examiner

ULTRASONIC IMAGING APPARATUS AND METHOD OF CONTROLLING THE SAME

CROSS-REFERENCE TO RELATED APPLICATION

This application is based on and claims priority under 35 U.S.C. § 119 to Korean Patent Application No. 2018-0088542, filed on Jul. 30, 2018 in the Korean Intellectual Property Office, the disclosure of which is incorporated herein by reference.

BACKGROUND

1. Field

The present disclosure relates to an ultrasonic imaging apparatus for generating an image of an internal part of a subject using ultrasonic waves, and a method of controlling the same.

2. Description of the Related Art

An ultrasonic imaging apparatus is an apparatus that radiates ultrasonic signals generated by a transducer of a probe toward a specific portion inside a subject from the body surface of the subject and acquires images of internal parts of the subject using information about reflected ultrasonic signals (ultrasonic echo signals).

The ultrasonic imaging apparatus has advantages in that it has high safety without exposure to X-rays or the like as compared to an X-ray diagnostic apparatus, is displayable in real time, and is inexpensive and portable as compared to a magnetic resonance imager (MRI), and therefore the ultrasonic imaging apparatus has been widely used for medical diagnoses.

SUMMARY

Therefore, it is an object of the present disclosure to provide an ultrasonic imaging apparatus capable of providing various types of information for diagnosing a subject using an ultrasonic image, and a method of controlling the same.

Additional aspects of the invention will be set forth in part in the description which follows and, in part, will be obvious from the description, or may be learned by practice of the invention.

Therefore, it is an aspect of the present invention to provide an ultrasonic imaging apparatus including: an inputter configured to receive an input of a region of interest (ROI) from a user; a beamformer configured to perform transmission/reception focusing with respect to a virtual source to be used for a synthetic aperture focusing method; and a main controller configured to determine a position of the virtual source on the basis of an image quality in the received ROI.

The ultrasonic imaging apparatus may further include a display, wherein the main controller may control the display to display the determined position of the virtual source.

The main controller may determine the position of the virtual source such that at least of a resolution or a contrast of the received ROI is greater than or equal to a predetermined reference value.

The main controller may determine the position of the virtual source on the basis of a number of beams synthesized in the received ROI.

The main controller may determine the position of the virtual source such that the position of the virtual source does not match a position of the received ROI.

The main controller may determine a lateral direction position of the virtual source in an ultrasonic image on the basis of the image quality in the received ROI.

The main controller may control the display to display a position of the received ROI and display the position of the virtual source together with the position of the ROI.

The main controller may control the display such that the position of the ROI is distinguished from the position of the virtual source.

The inputter may receive an input of changing the ROI from the user, wherein the main controller may change the position of the virtual source on the basis of an image quality of the changed ROI, and control the display to display the changed position of the virtual source.

It is another aspect of the present invention to provide a method of controlling an ultrasonic imaging apparatus, the method including: receiving an input of a region of interest (ROI) from a user; and performing transmission/reception focusing with respect to a virtual source to be used for a synthetic aperture focusing method; and determining a position of the virtual source on the basis of an image quality in the received ROI.

The method may further include displaying the determined position of the virtual source.

The determining of the position of the virtual source may include determining the position of the virtual source such that at least of a resolution or a contrast of the received ROI is greater than or equal to a predetermined reference value.

The determining of the position of the virtual source may include determining the position of the virtual source on the basis of a number of beams synthesized in the received ROI.

The determining of the position of the virtual source may include determining the position of the virtual source such that the position of the virtual source does not match a position of the received ROI.

The determining of the position of the virtual source may include determining a lateral direction position of the virtual source in an ultrasonic image on the basis of the image quality in the received ROI.

The displaying of the determined position of the virtual source may include displaying a position of the received ROI and displaying the position of the virtual source together with the position of the ROI.

The displaying of the determined position of the virtual source may include displaying the position of the ROI to be distinguished from the position of the virtual source.

The method may further include receiving an input of changing the ROI from the user; changing the position of the virtual source on the basis of an image quality of the changed ROI; and displaying the changed position of the virtual source.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Like numerals refer to like elements throughout the specification. Not all elements of embodiments of the present disclosure will be described, and description of what are commonly known in the art or what overlap each other in the embodiments will be omitted. The terms as used throughout the specification, such as "~part", "~module", "~member", "~block", etc., may be implemented in software and/or hardware, and a plurality of "~parts", "~modules", "~members", or "~blocks" may be implemented in a single element, or a single "~part", "~module", "~member", or "~block" may include a plurality of elements.

It will be further understood that the term "connect" or its derivatives refer both to direct and indirect connection, and the indirect connection includes a connection over a wireless communication network.

It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof, unless the context clearly indicates otherwise.

Although the terms "first," "second," "A," "B," etc. may be used to describe various components, the terms do not limit the corresponding components, but are used only for the purpose of distinguishing one component from another component.

As used herein, the singular forms "a," "an" and "the" are intended to include the plural forms as well, unless the context clearly indicates otherwise.

Reference numerals used for method steps are just used for convenience of explanation, but not to limit an order of the steps. Thus, unless the context clearly dictates otherwise, the written order may be practiced otherwise.

Hereinafter, the principles and embodiments of the disclosure will be described with reference to the accompanying drawings.

Figure 1:
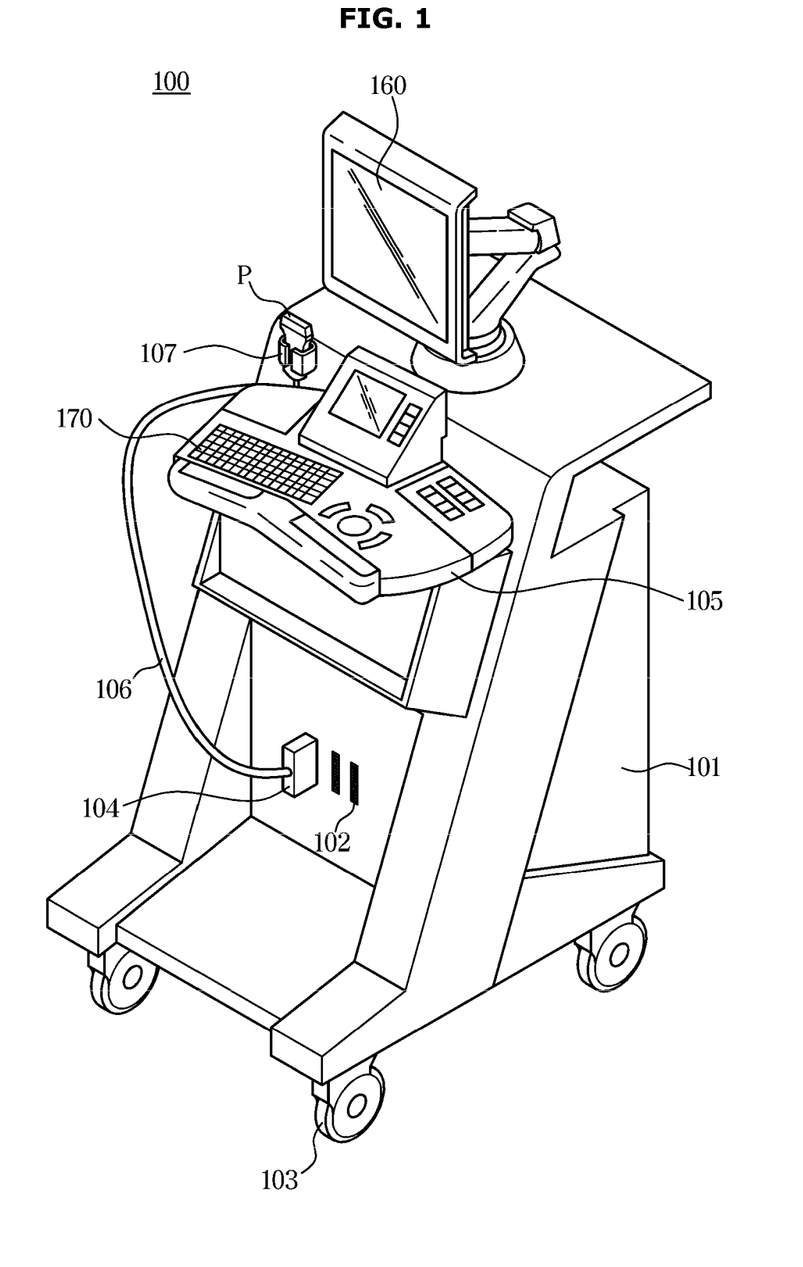
FIG. 1 is a view illustrating an external appearance of an ultrasonic imaging apparatus according to an embodiment.
Figure 2:
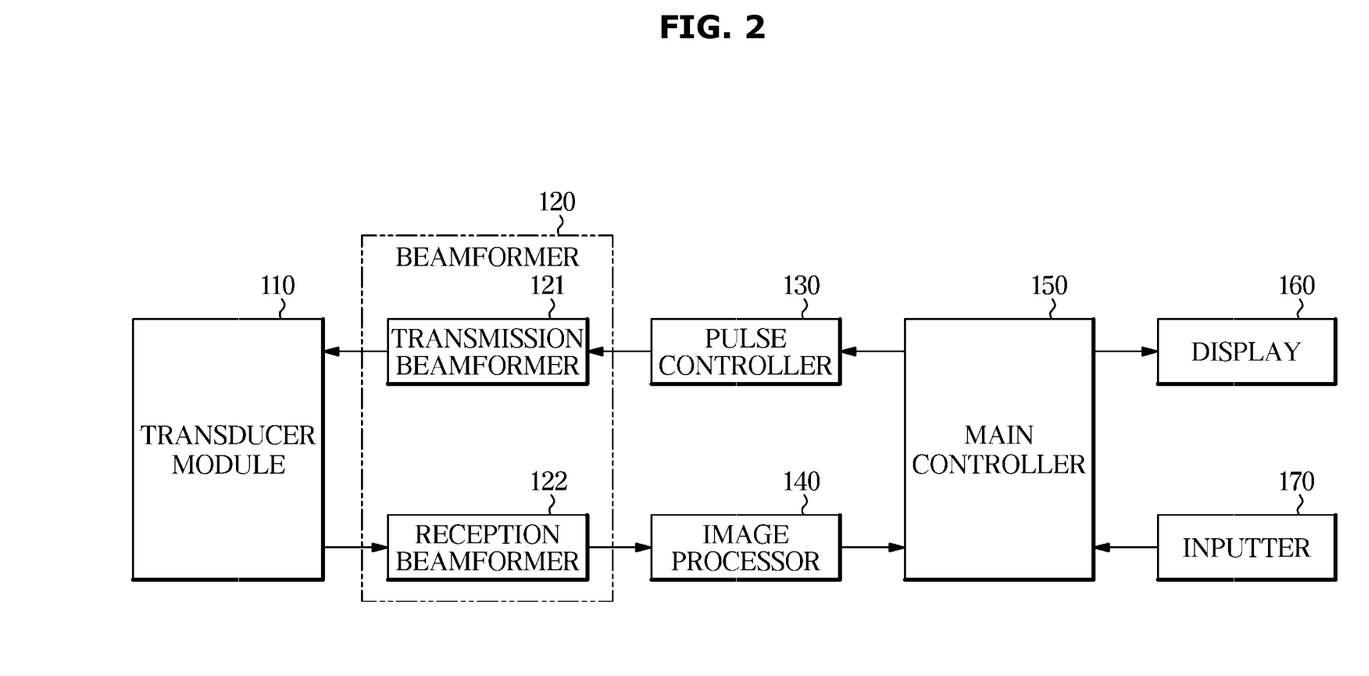
FIG. 2 is a control block diagram illustrating an ultrasonic imaging apparatus according to an embodiment.

FIG. 1 is a view illustrating an external appearance of an ultrasonic imaging apparatus according to an embodiment, and FIG. 2 is a control block diagram illustrating an ultrasonic imaging apparatus according to an embodiment.

Referring to FIGS. 1 and 2, an ultrasonic imaging apparatus 100 according to an embodiment includes a transducer module 110 for performing conversion between an electrical signal and an ultrasonic signal, a beamformer 120 for generating a transmission beam and a reception beam, a pulse controller 130 for generating a control signal for generating a pulse and transmitting the control signal to the beamformer 120, an image processor 140 for generating an ultrasonic image using an echo signal output from the beamformer 120, a main controller 150 for controlling the overall operation of the ultrasonic imaging apparatus 100, a display 160 for displaying the generated ultrasonic image and various types of data required for diagnosis, and an inputter 170 for receiving an input of a user.

The transducer module 110 may be provided inside an ultrasonic probe P, and the ultrasonic probe P may be connected to a main body 101 of the ultrasonic imaging apparatus 100 through a cable 106.

To this end, one or more female connectors 102 may be provided on a front lower side of the main body 101. A male connector 104 provided at one end of the cable 106 may be physically coupled to the female connector 102.

A plurality of casters 103 for moving the ultrasonic imaging apparatus 100 may be provided in a lower portion of the main body 101. The user may fix or move the ultrasonic imaging apparatus 100 using the plurality of casters 103. Such an ultrasonic imaging apparatus 100 is referred to as a cart-type ultrasonic apparatus.

A control panel 105 may be provided on the front side of the main body 101. The control panel 105 may include an inputter 170 for receiving a user's input and a user may input commands to start diagnosis, select a diagnosis area, select a diagnosis type, select a mode of an ultrasonic image, and the like. Examples of the mode of the ultrasonic image may include an amplitude mode (A-mode), a brightness mode (B-mode), a doppler mode (D-mode), an elastography mode (E-mode), or a motion mode (M-mode).

The main body 101 is provided on an upper side thereof with the display 160. The display 160 may be implemented using at least one of a liquid crystal display (LCD) panel, a light emitting diode (LED) panel, an organic light emitting diode (OLED), or other various display panels.

In addition, the display 160 may include two or more displays such that the respective displays simultaneously display different images. For example, one display may display a two-dimensional (2D) ultrasonic image and another display may display a three-dimensional (3D) ultrasonic image. Alternatively, one display may display a B-mode image, and another display may display a contrast agent image.

The main body 101 is provided on an outer circumferential surface thereof with one or more probe holders 107 for holding the ultrasonic probe P. Accordingly, the user may place and store the ultrasonic probe P in the probe holder 107 while the ultrasonic probe P is not in use.

On the other hand, the beamformer 120 may be provided in the main body 101 or may be provided in the ultrasonic probe P according to embodiments. Although the beamformer 120 according to the disclosed embodiment is illustrated as being separated from the ultrasonic probe P and provided in the main body 101, the embodiment of the ultrasonic imaging apparatus 100 is not limited thereto.

The main body 101 may have the pulse controller 130, the image processer 140, and the main controller 150 embedded therein. The pulse controller 130, the image processer 140, and the main controller 150 each may include at least one memory for storing a program for performing an operation, which will be described below, and at least one processor for executing the stored program. Each of the pulse controller 130, the image processer 140, and the main controller 150 may use a separate memory and a separate processor, or may use a memory and a processor shared therebetween.

On the other hand, the external appearance of the ultrasonic imaging apparatus 100 according to the embodiment is not limited to the example shown in FIG. 2, and the ultrasonic imaging apparatus 100 may be implemented in a portable type. When the ultrasonic imaging apparatus 100 is implemented in a portable type, the main body 101 may have a form, such as a laptop computer, a personal digital assistant (PDA), a tablet PC, or the like, and may generate an ultrasonic image by connecting the ultrasonic probe P to the main body 101.

Figure 3:
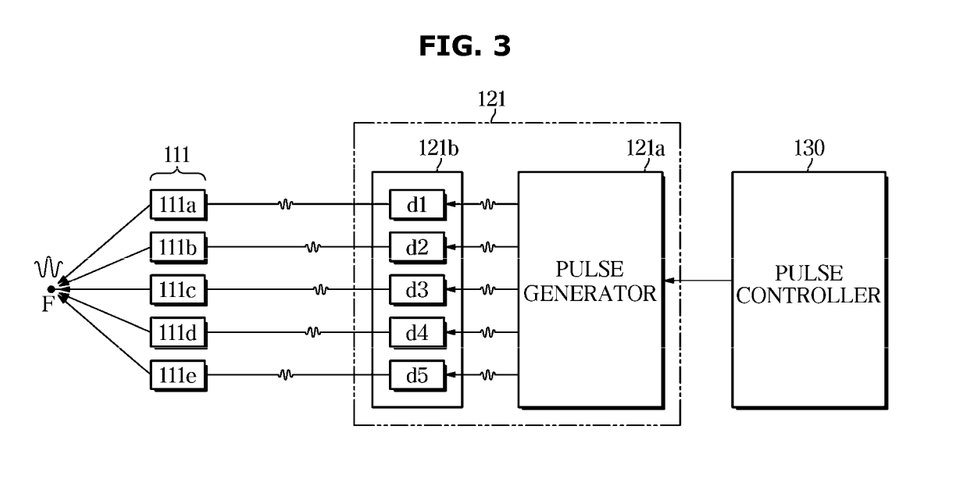
FIG. 3 is a view for describing a process of transmitting ultrasonic waves.
Figure 4:
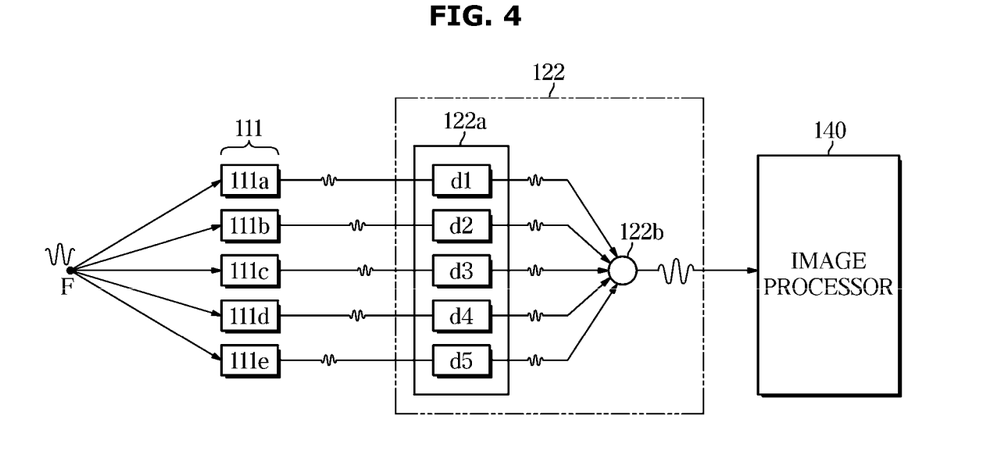
FIG. 4 is a view for describing a process of receiving ultrasonic waves.

FIG. 3 is a view for describing a process of transmitting ultrasonic waves, and FIG. 4 is a view for describing a process of receiving ultrasonic waves.

Referring to FIGS. 3 and 4, the transducer module 110 may include a transducer array 111 composed of a plurality of transducer elements, and may further include a switch, such as a multiplexer (MUX) for selecting a transducer element to be used for transmitting and receiving ultrasonic signals.

For the sake of convenience in description, the following description will be made in relation to the transducer array 111 including five transducer elements 111*a*, 111*b*, 111*c*, 111*d*, and 111*e* as an example.

The transducer elements 111 may perform conversion between an ultrasonic signal and an electric signal. For example, the transducer element 111 may be implemented as a piezoelectric ultrasonic transducer using a piezoelectric effect. To this end, the transducer element 111 may include a piezoelectric material or a piezoelectric thin film. When an alternating current is applied from an internal power storage device, such as a battery, or an external power supply device, to the piezoelectric material or piezoelectric thin film, the piezoelectric material or piezoelectric thin film vibrates at a predetermined frequency and ultrasonic waves of a predetermined frequency are generated according to the vibration frequency.

On the contrary, when ultrasonic echo waves of a predetermined frequency reach the piezoelectric material or piezoelectric thin film, the piezoelectric material or piezoelectric thin films vibrate according to the frequency of the ultrasonic echo waves and output alternating current of a frequency corresponding to the vibration frequency thereof.

In addition, the transducer element 111 may be implemented using, for example, any one of a magnetostrictive ultrasonic transducer using a magnetostrictive effect of a magnetic body, a capacitive micromachined ultrasonic transducer (cMUT), which transmits and receives ultrasonic waves using vibration of several hundreds or several thousands of micromachined thin films, or other types of transducers.

Referring to FIG. 1, the beam former 120 may include a transmission beamformer 121 and a reception beamformer 122.

The transmission beamformer 121 performs transmission beamforming. Referring to FIG. 3, distances between each of the plurality of transducer elements 111*a*, 111*b*, 111*c*, 111*d* and 111*e* and a focus F are different. Therefore, the transmission beamformer 121 may generate a transmission beam by assigning time delays such that ultrasonic signals transmitted from the respective transducer elements 111*a*, 111*b*, 111*c*, 111*d* and 111*e* simultaneously reach a focus F of a transmission scan line. When the width of the ultrasonic beam is narrowed through the focusing of the ultrasonic signals, the lateral direction resolution may be improved.

The transmission beamformer 121 may include a pulse generator 121*a* and a first delay 121*b*.

The pulse generator 121*a* generates a pulse according to a control signal of the pulse controller 130. For example, the pulse generated by the pulse generator 121*a* may be a pulse having a pulse repetition frequency (PRF). The pulse generated by the pulse generator 121*a* is input to the first delay 121*b*.

The first delay 121*b* delays each pulse output from the pulse generator 121*a* by a predetermined time, and outputs the delayed pulse. The first delay 121*b* may include a plurality of delay elements d1 to d5, and the plurality of delay elements d1 to d5 may be connected to the transducer elements 111*a* to 111*e*, respectively.

The delay times of the delay elements d1 to d5 are determined by the distances between each of the transducer elements 111*a* to 111*e* and the focus F. That is, in order that when ultrasonic signals transmitted from a first transducer element 111*a* and a fifth transducer element 111*e*, which are distant from the focus F, reach the focus F, ultrasonic waves transmitted from second to fourth transducer elements 111*b* to 111*d* reach the focus F, second to fourth delay elements d2 to d4 delay input pulses by a predetermined time and output the delayed pulses.

As described above, the ultrasonic waves transmitted through the transducer array 111 are reflected by a subject and are incident on the transducer array 111 again. In response to receiving such ultrasonic echo waves reflected from the subject, the transducer elements 111*a* to 111*e* output echo signals corresponding to the received ultrasonic echo waves. The echo signals output as such are input to the reception beamformer 122.

Referring to FIG. 4, the reception beamformer 122 includes a second delay 122*a* and a synthesizer 122*b*. Although not shown in the drawings, the reception beamformer 122 may further include a receiver for receiving an echo signal and performing amplification and gain correction on the received echo signal, and when the reception beamformer 122 is implemented as a digital beamformer, the reception beamformer 122 may further include an analog-to-digital converter (ADC) to convert an analog echo signal subjected to the amplification and gain correction into a digital echo signal.

The second delay 122*a* may include a plurality of delay elements d1 to d5, and the delay elements d1 to d5 may be connected to the transducer elements 111*a* to 111*e*, respectively.

Since the times at which the ultrasonic echo waves reach the respective transducer elements 111*a* to 111*e* are different from each other, each of the delay elements d1 to d5 delays a corresponding input echo signal by a predetermined time to focus the echo signals and outputs the delayed echo signal.

For example, a third delay element d3 to which an echo signal is input first delays the input echo signal until echo signals are input to first and fifth delay elements d1 and d5, and outputs the delayed echo signal.

As described above, the ultrasonic signals output from the plurality of transducer elements 111*a*, 111*b*, 111*c*, 111*d*, and 111*e* may be controlled to have the same phase at a time of reaching a first focus F inside a subject 20 on the basis of the different transmission delay times. Such a focusing of a plurality of ultrasonic signals to the first focus F may be defined as a transmission focusing. However, the above-described transmission focusing is merely one example of this embodiment of the present disclosure, but those skilled in the art will appreciate that various modified embodiments are possible.

Generally, dynamic transmission focusing refers to focusing ultrasonic signals to a plurality of focuses or a plurality of image points located in one scan line multiple times.

Whereas, the dynamic transmission focusing may be effectively performed by focusing ultrasonic signals to different focuses on different scan lines and by assuming signals reflected from the different focuses as virtual sources to acquire ultrasonic signals. Such a scheme of acquiring ultrasonic signals through a plurality of virtual sources may be represented by a synthetic aperture focusing method.

The synthetic aperture focusing method may include a bi-directional pixel based focusing method in which a virtual source is positioned in front of a probe and a spherical wave propagates forward and backward of the virtual source.

The synthesizer 122*b* synthesizes echo signals output from the delay elements d1 to d5. In this case, the synthesizer 212 may assign weights to the echo signals and synthesize the weighted echo signals.

The image processor 140 generates an ultrasonic image on the basis of the echo signals output from the reception beamformer 122. For example, the image processer 140 may generate at least one of an A-mode image, a B-mode image, a D-mode image, an E-mode image, or an M-mode image on the basis of the echo signals. In addition, the image processor 140 may generate a 3D ultrasonic image on the basis of a plurality of ultrasonic images acquired from the echo signals.

The main controller 150 may determine the position of a virtual source at which ultrasonic signals are to be focused, and control the beamformer 120 to perform transmission and reception focusing on the determined position of the virtual source.

In addition, the main controller 150 may control the display 160 to display the position of a virtual source, and may control the display 160 to display the position of a region of interest (ROI) received from the user. To this end, the user may input an ROI through the inputter 170, and the ROI refers to a region of an ultrasonic image that the user desires to observe.

In addition, the ultrasonic imaging apparatus 100 according to the embodiment may further include a storage (not shown) for storing the position of the received ROI and the position of the virtual source determined in response to the received ROI.

Figure 5A:
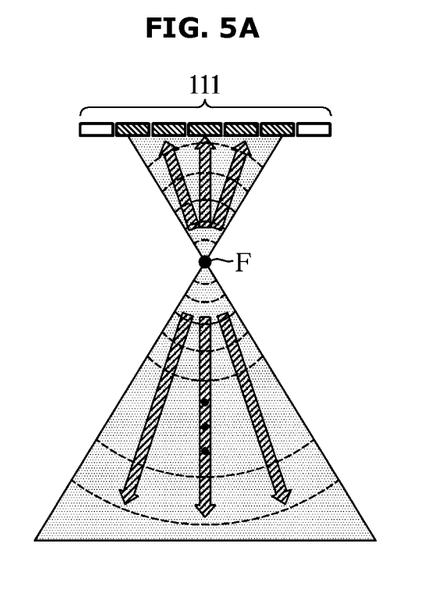
FIGS. 5A and 5B are views for describing an operation of focusing ultrasonic signals by an ultrasonic imaging apparatus according to an embodiment.
Figure 5B:
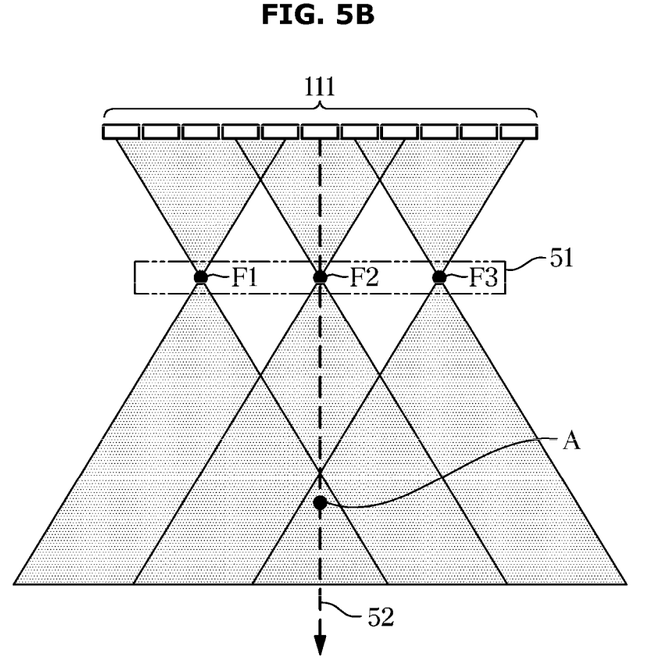

FIGS. 5A and 5B are views for describing an operation of focusing ultrasonic signals by an ultrasonic imaging apparatus according to an embodiment.

Referring to FIG. 5A, it is assumed that each beam including ultrasonic signals synthesized to generate an ultrasonic image spreads from one point.

That is, when the ultrasonic signals from the transducer elements 111 are focused to one focus F, the beam width is gradually narrowed from the transducer elements 111 to a focus F, and after reaching the focus F, the beam width may be gradually widen. In this case, the focus F may be analyzed as a virtual source.

The ultrasonic signal transmitted from the transducer element 111 and the received ultrasonic signal may have information about all the regions that the transmitted ultrasonic signal reaches. In this case, when the beam width is sufficiently spread wide, information about image points on other scan lines may be included in the information.

Referring to FIG. 5B, three virtual sources F1, F2, and F3 may form a virtual aperture 51. For example, a first virtual source F1, a second virtual source F2, and a third virtual source F3 may form the same virtual aperture 51. In this case, the virtual sources F1, F2, and F3 forming the same virtual aperture 51 may have the same positions in an axis of a lateral direction composed of scan lines.

In this case, with respect to an image point A on a scan line 52, the three beams may include the corresponding image point A. Since different beams all include the same image point A, information about the image point A may be included in signals transmitted and received at different apertures.

Information included in echo signals from the different beams may be synthesized, and the image processor 140 may generate an image with respect to the corresponding image point A on the basis of the synthesized information.

As the number of beams passing through a specific image point increases, that is, as the number of beams synthesized for image generation increases, the spatial resolution for an image at the specific image point may be improved.

On the other hand, even when the number of beams to be synthesized is the same, the spatial resolution may decrease as the distance between the image point and the virtual source is increased. Therefore, it is crucial to determine the position of the virtual source that may secure the optimum spatial resolution while maximizing the degree to which beams are synthesized for a specific region.

The main controller 150 may determine the position of the virtual source on the basis of the image quality in an ROI that the user desires to observe. That is, the main controller 150 may determine the position of the virtual source that may maximize the image quality of the ultrasonic image in the ROI. In this case, the position of the virtual source refers to a position in the axis in the lateral direction composed of scan lines.

In detail, the main controller 150 may determine the position of the virtual source that may maximize at least one of the resolution or the contrast of the ultrasonic image with respect to the ROI that the user desires to observe.

For example, the main controller 150 may determine the position of the virtual source in which at least one of the resolution or the contrast in the ROI is equal to or greater than a predetermined reference value.

In addition, as described above, since the resolution and the contrast of an image for an ROI may be increased as the number of beams to be synthesized in the ROI increases, the main controller 150 may determine the position of the virtual source on the basis of the number of beams to be synthesized in the ROI.

In addition, since the resolution of an image may be lowered as the distance between the ROI and the virtual source increases, the main controller 150 may determine the position of the virtual source on the basis of the distance between the ROI and the virtual source.

In addition, the main controller 150 may determine the position of the virtual source on the basis of both the number of beams synthesized in the ROI and the distance between the ROI and the virtual source.

As described above, when the position of the virtual source is determined, the main controller 150 may store the determined position of the virtual source. The main controller 150 may store the positions of virtual sources for respective input ROIs.

When an ROI is input, the main controller 150 may check whether an ROI having the same position as that of the input ROI is stored, and when the ROI having the same position as that of the input ROI is stored, the main controller 150 may determine the position of the virtual source on the basis of a position of a virtual source corresponding to the ROI, which has the same position as that of the input ROI, among the stored positions of virtual sources.

Figure 6A:
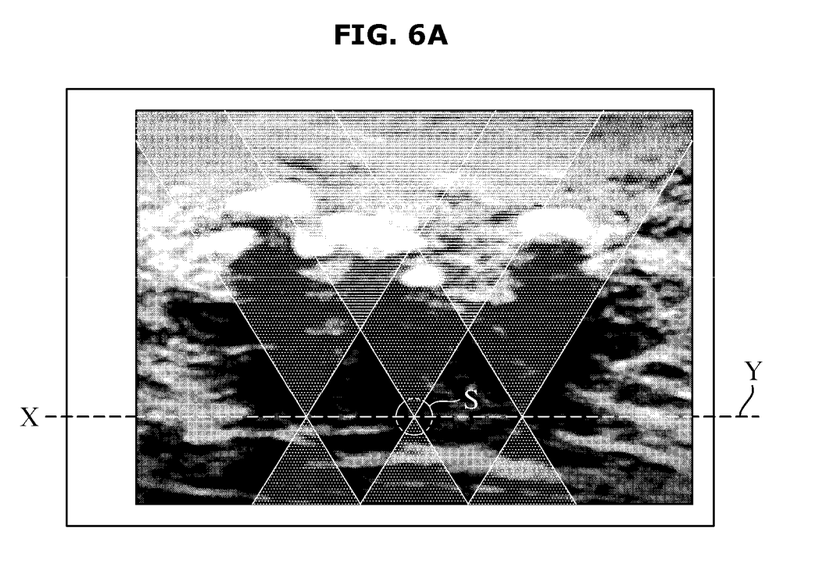
FIG. 6A is a view for describing an operation of determining the position of a virtual source by the conventional ultrasonic imaging apparatus.
Figure 6B:
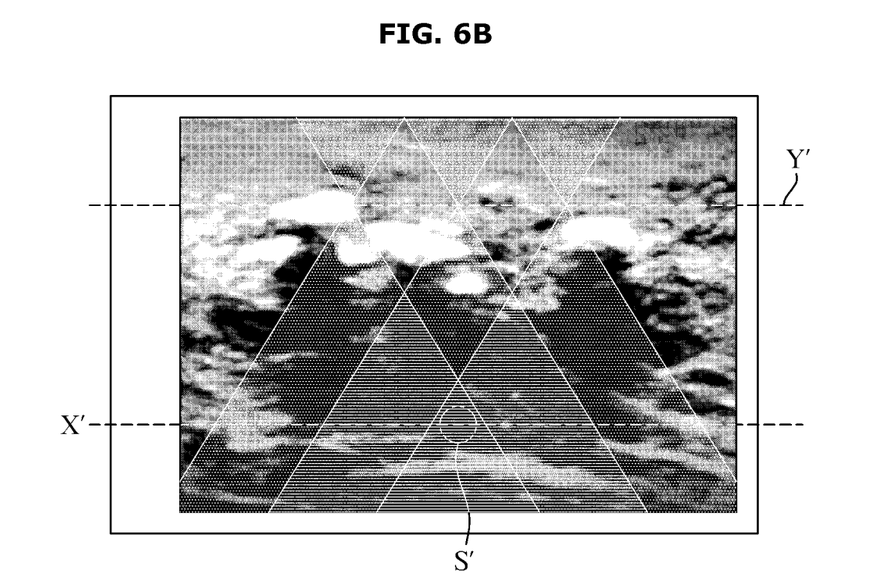
FIG. 6B is a view for describing an operation of determining the position of a virtual source by an ultrasonic imaging apparatus according to an embodiment.

FIG. 6A is a view for describing an operation of determining the position of a virtual source by the conventional ultrasonic imaging apparatus, and FIG. 6B is a view for describing an operation of determining the position of a virtual source by an ultrasonic imaging apparatus according to an embodiment.

Referring to FIG. 6A, the conventional ultrasonic imaging apparatus places a virtual source at a position X selected by the user such that the beam is focused to the position of the virtual source. That is, the position X selected by the user is the same as a position Y of the virtual source, and the ultrasonic imaging apparatus places the virtual source at the position X selected by the user and focuses the beam to the corresponding position to generate an image.

When the beam is focused according to the synthetic aperture focusing method, the beam is focused to the position X selected by the user, and a region adjacent to the position X may not be subjected to sufficient beam synthesis, leading to a lower image quality compared to other regions.

In other words, the position selected by the user in the conventional ultrasonic imaging apparatus is not a position in which the image quality is maximized, and in order to increase the image quality of the ultrasonic image for an ROI S desired to be observed, the user needs to directly adjust the position Y of the virtual source.

Since the region directly selected by the user in the conventional ultrasonic imaging apparatus is a region of a virtual source rather than an ROI S, there is inconvenience of the user needing to directly adjust the position Y of the virtual source while checking the image quality of the ROI S.

Referring to FIG. 6B, with the ultrasonic imaging apparatus 100 according to the embodiment, the user may select an ROI S' desired to be observed through the inputter 170. That is, the ultrasonic imaging apparatus 100 according to the embodiment may receive the region S' selected by the user as an ROI.

The main controller 150 may obtain a position Y' of a virtual source on the basis of the image quality of the ultrasonic image with respect to the input ROI S'. In this case, the position of the virtual source refers to a position in the axis in the lateral direction composed of scan lines.

In detail, the main controller 150 may calculate the position Y' of the virtual source such that the image quality of the ultrasonic image with respect to the inputted ROI S' is maximized.

In this case, the position Y' of the virtual source for maximizing the image quality of the ultrasonic image with respect to the ROI S' may be determined on the basis of at least one of the resolution or the contrast of the ultrasonic image for the ROI S'.

For example, the main controller 150 may calculate the position Y' of the virtual source that allows at least one of the resolution or the contrast of the ultrasonic image with respect to the ROI S' to have the maximum value. Alternatively, the main controller 150 may calculate the position Y' of the virtual source that allows at least one of the resolution and the contrast of the ultrasonic image with respect to the ROI S' to be equal to or greater than a predetermined reference value.

In addition, the position Y' of the virtual source allowing the image quality of the ultrasonic image with respect to the ROI S' to be maximized may be determined on the basis of at least one of the number of beams synthesized in the ROI S' or the distance between the ROI and the virtual source.

For example, the main controller 150 may acquire a position at which the number of beams synthesized in the ROI S' is maximized as the position of the virtual source, or may acquire a position at which the virtual source is the nearest to the ROI S' as the position of the virtual source. Alternatively, the main controller 150 may acquire a position at which the number of beams synthesized in the ROI S' is maximized and the virtual source is the nearest to the ROI S' as the position of the virtual source.

As described above, the position X' of the ROI S that the user desires to observe in the ultrasonic imaging apparatus 100 according to the embodiment does not coincide with the position Y' of the virtual source. That is, the region S' selected by the user through the inputter 170 is input as an ROI S rather than the position of the virtual source.

Accordingly, since the position Y' of the virtual source, which allows the image quality of the ultrasonic image in the region S' selected by the user to be increased, is automatically acquired, the user may acquire an ultrasonic image having an increased image quality for the selected region without needing to directly adjust the position of the virtual source.

In addition, since the region S selected by the user through the inputter 170 is input as an ROI, and the position of the optimal virtual position for the region is automatically obtained, the user may intuitively select the region to be observed, thereby increasing the user convenience.

Figure 7:
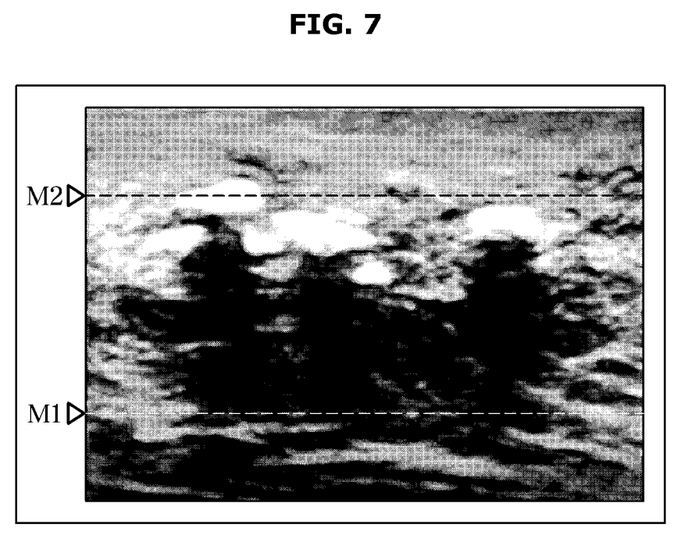
FIG. 7 is a view illustrating an example of a screen displayed on an ultrasonic imaging apparatus according to an embodiment.

FIG. 7 is a view illustrating an example of a screen displayed on an ultrasonic imaging apparatus according to an embodiment.

Referring to FIG. 7, the ultrasonic imaging apparatus 100 according to the embodiment may display the determined position of the virtual source.

The main controller 150 may control the display 160 to display the position of the virtual source.

For example, the main controller 150 may control the display 160 to display the position of the virtual source using at least one of an icon, an image, or text.

In addition, the main controller 150 may control the display 160 to display the position of the virtual source in various forms, for example, using a marker without being limited to the above example.

In addition, the main controller 150 may control the display 160 to display the position of the virtual source together with the position of the ROI received from the user.

For example, as shown in FIG. 7, the main controller 150 may display a position M1 of an ROI received from the user to be distinguished from a determined position M2 of a virtual source. To this end, the main controller 150 may control the display 160 to display the position of the ROI and the position of the virtual source using different colors, shapes, texts, or the like.

In addition, when the user changes the position M1 of the ROI, the main controller 150 may display the position of the ROI changed, and may change the position of the virtual source such that the previously displayed position M2 of the virtual source is linked with the position of the ROI changed.

Figure 8:
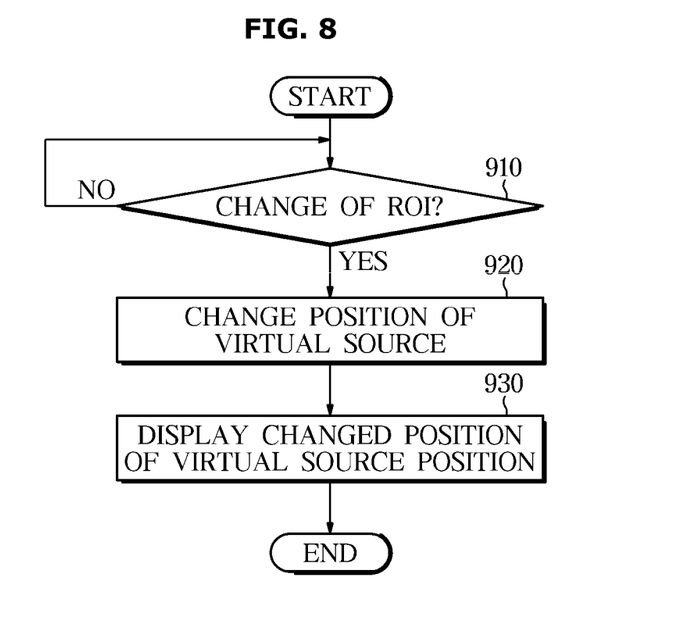
FIG. 8 is a flowchart showing a method of controlling an ultrasonic imaging apparatus according to an embodiment.

FIG. 8 is a flowchart showing a method of controlling an ultrasonic imaging apparatus according to an embodiment.

Referring to FIG. 8, the ultrasonic imaging apparatus 100 according to the embodiment may check whether an input from a user exists (810). In this case, the user may input a region to be observed, and the ultrasonic imaging apparatus 100 may receive the region to be observed, that is, the position of a region of interest (ROI), as an input value.

When an input from the user exists (YES in 810), the ultrasonic imaging apparatus 100 may determine the position of a virtual source (820).

In detail, the ultrasonic imaging apparatus 100 may determine the position of the virtual source for employing the synthetic aperture focusing method on the basis of the image quality of the ultrasonic image in the region received from the user. That is, the main controller 150 may determine the position of the virtual source that allows the image quality of the ultrasonic image in the ROI to be maximized. In this case, the position of the virtual source refers to a position in the axis in the lateral direction composed of scan lines.

The determining of the position of the virtual source that allows the image quality of the ultrasonic image to be maximized may include determining the position of the virtual source that allows at least one of the resolution or the contrast of the ultrasonic image with respect to the ROI to be maximized. In addition, the determining of the position of the virtual source that allows the image quality of the ultrasonic image to be maximized may include determining the position of the virtual source in which the number of beams synthesized in the ROI is great, or determining the position of the virtual source at which the virtual source is near to the ROI.

When the position of the virtual source is determined, the ultrasonic imaging apparatus 100 may display the determined position of the virtual source (830). In this case, the ultrasonic imaging apparatus 100 display the position of the virtual source together with the position of the ROI received from the user.

In this case, the region received from the user is recognized as an ROI desired to be observed by the user, rather than the position of a virtual source, and such a position of a virtual source that allows the image quality of the ROI to be maximized may be automatically determined.

Accordingly, the user may intuitively input the ROI that the user desires to observe, regardless of the position of the virtual source, and may obtain the optimal image quality of the input region without needing to consider the position of the virtual source, thereby increasing the convenience of use.

Figure 9:
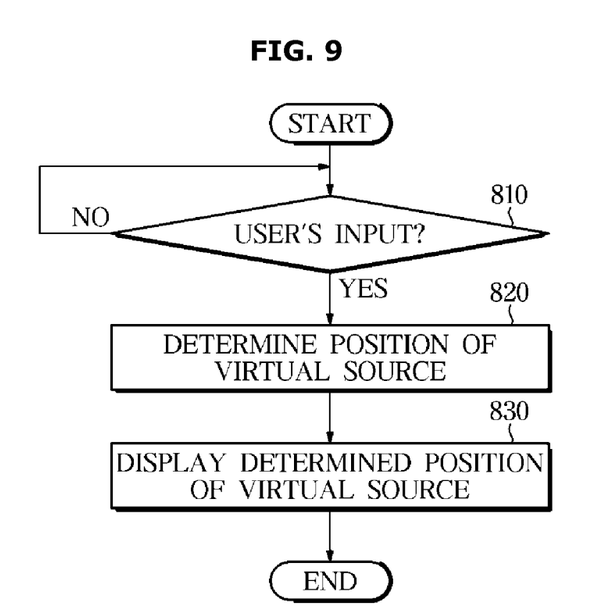
FIG. 9 is a flowchart showing a method of controlling an ultrasonic imaging apparatus according to an embodiment.

FIG. 9 is a flowchart showing a method of controlling an ultrasonic imaging apparatus according to an embodiment.

Referring to FIG. 9, the ultrasonic imaging apparatus 100 according to the embodiment may check whether the ROI is changed (910). In detail, when the position of the ROI input from the user is changed, the ultrasonic imaging apparatus 100 may determine that the ROI has been changed.

When a change of the ROI occurs (YES in 910), the ultrasonic imaging apparatus 100 may change the position of the virtual source (920). The ultrasonic imaging apparatus 100 may change the position of the virtual source to be linked with position of the ROI changed. In detail, the ultrasonic imaging apparatus 100 may change the position of the virtual source on the basis of the image quality of the ultrasonic image in the position of the ROI changed.

When the position of the virtual source is changed, the ultrasonic imaging apparatus 100 may display the changed position of the virtual source position (930). In this case, the ultrasonic imaging apparatus 100 may shift the previously displayed position of the virtual source to the changed position of the virtual source.

While displaying the changed position of the virtual source, the ultrasonic imaging apparatus 100 may display the position of the ROI changed.

As described above, in a state in which the position of the ROI and the position of the virtual source are displayed, when the user changes the ROI, the ultrasonic imaging apparatus 100 may allow the displayed position of the virtual source to be linked with the position of the ROI changed.

As is apparent from the above, the vehicle and the method of controlling the same according to the aspect of the present invention can increase the user convenience and prevent hacking by authenticating a user terminal in consideration of a specific usage environment in which a user uses the user terminal.

Although exemplary embodiments of the present disclosure have been described for illustrative purposes, those skilled in the art will appreciate that various modifications, additions and substitutions are possible, without departing from the scope and spirit of the disclosure. Therefore, exemplary embodiments of the present disclosure have not been described for limiting purposes.

What is claimed is:

1. An ultrasonic imaging apparatus comprising:
   an inputter configured to receive an input of a region of interest (ROI) from a user;
   a beamformer configured to perform transmission/reception focusing with respect to a virtual source to be used for a synthetic aperture focusing method; and
   a main controller configured to determine a position of the virtual source on the basis of an image quality in the received ROI.

2. The ultrasonic imaging apparatus of claim 1, further comprising a display,
   wherein the main controller controls the display to display the determined position of the virtual source.

3. The ultrasonic imaging apparatus of claim 1, wherein the main controller determines the position of the virtual source such that at least of a resolution or a contrast of the received ROI is greater than or equal to a predetermined reference value.

4. The ultrasonic imaging apparatus of claim 1, wherein the main controller determines the position of the virtual source on the basis of a number of beams synthesized in the received ROI.

5. The ultrasonic imaging apparatus of claim 1, wherein the main controller determines the position of the virtual source such that the position of the virtual source does not match a position of the received ROI.

6. The ultrasonic imaging apparatus of claim 1, wherein the main controller determines a lateral direction position of the virtual source in an ultrasonic image on the basis of the image quality in the received ROI.

7. The ultrasonic imaging apparatus of claim 2, wherein the main controller controls the display to display a position of the received ROI and display the position of the virtual source together with the position of the ROI.

8. The ultrasonic imaging apparatus of claim 7, wherein the main controller controls the display such that the position of the ROI is distinguished from the position of the virtual source.

9. The ultrasonic imaging apparatus of claim 7, wherein the inputter receives an input of changing the ROI from the user,
   wherein the main controller changes the position of the virtual source on the basis of an image quality of the changed ROI, and controls the display to display the changed position of the virtual source.

10. A method of controlling an ultrasonic imaging apparatus, the method comprising:
    receiving an input of a region of interest (ROI) from a user; and performing transmission/reception focusing with respect to a virtual source to be used for a synthetic aperture focusing method; and determining a position of the virtual source on the basis of an image quality in the received ROI.

11. The method of claim 10, further comprising displaying the determined position of the virtual source.

12. The method of claim 10, wherein the determining of the position of the virtual source includes determining the position of the virtual source such that at least of a resolution or a contrast of the received ROI is greater than or equal to a predetermined reference value.

13. The method of claim 10, wherein the determining of the position of the virtual source includes determining the position of the virtual source on the basis of a number of beams synthesized in the received ROI.

14. The method of claim 10, wherein the determining of the position of the virtual source includes determining the position of the virtual source such that the position of the virtual source does not match a position of the received ROI.

15. The method of claim 10, wherein the determining of the position of the virtual source includes determining a lateral direction position of the virtual source in an ultrasonic image on the basis of the image quality in the received ROI.

16. The method of claim 11, wherein the displaying of the determined position of the virtual source includes displaying a position of the received ROI and displaying the position of the virtual source together with the position of the ROI.

17. The method of claim 16, wherein the displaying of the determined position of the virtual source includes displaying the position of the ROI to be distinguished from the position of the virtual source.

18. The method of claim 16, further comprising receiving an input of changing the ROI from the user;

changing the position of the virtual source on the basis of an image quality of the changed ROI; and displaying the changed position of the virtual source.

* * * * *